(12) United States Patent
Shin et al.

(10) Patent No.: US 10,806,799 B2
(45) Date of Patent: Oct. 20, 2020

(54) HUMAN INTERFERON-BETA VARIANT CONJUGATED IMMUNOCYTOKINE AND METHOD FOR PREPARING SAME

(71) Applicant: GenoPharm Inc., Seoul (KR)

(72) Inventors: Young Kee Shin, Seoul (KR); Young Deug Kim, Incheon (KR); Jun Young Choi, Gwangmyeong-si (KR); Tae Eun Kim, Anyang-si (KR); Young Jin Lee, Seoul (KR); Ju Ho Lee, Seoul (KR); Yeong Mun Kim, Bucheon-si (KR)

(73) Assignee: GENOPHARM INC., Seoul (KR)

( * ) Notice: Subject to any disclaimer, the term of this patent is extended or adjusted under 35 U.S.C. 154(b) by 76 days.

(21) Appl. No.: 15/693,148

(22) Filed: Aug. 31, 2017

(65) Prior Publication Data

US 2018/0236092 A1   Aug. 23, 2018

Related U.S. Application Data

(63) Continuation-in-part of application No. PCT/KR2016/002129, filed on Mar. 3, 2016.

(30) Foreign Application Priority Data

Mar. 3, 2015 (KR) .................. 10-2015-0030037

(51) Int. Cl.

| | |
|---|---|
| *A61K 47/64* | (2017.01) |
| *A61K 47/68* | (2017.01) |
| *C07K 16/28* | (2006.01) |
| *C07K 16/32* | (2006.01) |
| *C07K 14/565* | (2006.01) |
| *C07K 16/30* | (2006.01) |
| *C07K 19/00* | (2006.01) |
| *C12N 15/63* | (2006.01) |
| *A61K 38/19* | (2006.01) |
| *A61K 38/21* | (2006.01) |

(52) U.S. Cl.
CPC ........ *A61K 47/642* (2017.08); *A61K 47/6813* (2017.08); *A61K 47/6845* (2017.08); *A61K 47/6849* (2017.08); *A61K 47/6851* (2017.08); *A61K 47/6875* (2017.08); *C07K 14/565* (2013.01); *C07K 16/2863* (2013.01); *C07K 16/30* (2013.01); *C07K 16/32* (2013.01); *C07K 19/00* (2013.01); *C12N 15/63* (2013.01); *A61K 38/19* (2013.01); *C07K 2317/14* (2013.01); *C07K 2317/30* (2013.01); *C07K 2319/00* (2013.01); *C07K 2319/31* (2013.01)

(58) Field of Classification Search
None
See application file for complete search history.

(56) References Cited

U.S. PATENT DOCUMENTS

2010/0003721 A1 * 1/2010 Shin .................... C07K 14/565
435/69.51

FOREIGN PATENT DOCUMENTS

| KR | 100511749 | 9/2005 |
|---|---|---|
| KR | 100781666 | 12/2007 |
| KR | 20100019467 | 2/2010 |
| KR | 20100084634 | 7/2010 |

OTHER PUBLICATIONS

Del Val et al., "Application of Quality by Design Paradigm to the Manufacture of Protein Therapeutics", Glycosylation, Intech, 2012, DOI: 10.5772/50261, p. 353-396.
Jayanthi et al., "Efficient production and purification of recombinant human interleukin-12 (IL-12) overexpressed in mammalian cells without affinity tag", Protein Expr Purif., 2014, 102: 76-84.
Sommavilla et al., "Expression, engineering and characterization of the tumor-targeting heterodimeric immunocytokine F8-IL12", Protein Engineering, Design & Selection, 2010, 23(8): 653-661.

* cited by examiner

*Primary Examiner* — Joanne Hama
*Assistant Examiner* — Jegatheesan Seharaseyon
(74) *Attorney, Agent, or Firm* — James S. Keddie; Bozicevic, Field & Francis LLP

(57) ABSTRACT

The present invention relates to an immunocytokine in which a human interferon-beta variant is conjugated to an antibody or a fragment thereof, and a method for preparing the same. The human interferon-beta variant has superior activity or functions compared with natural interferon-beta, and the productivity of the immunocytokine according to the present invention is excellent. In addition, the immunocytokine according to the present invention can be favorably used as a target therapeutic agent for multiple sclerosis or cancer since the immunocytokine express both of functions of the interferon-beta and characteristics of the antibody binding to a specific antigen.

10 Claims, 9 Drawing Sheets

Specification includes a Sequence Listing.

Western Blot: anti-Human IgG

1. Heavy Chain-linker-INF-β + Light Chain
2. Heavy Chain-linker- Carbiferon + Light Chain Western Blot: anti-Interferon-β

1. Heavy Chain-linker-INF-β + Light Chain
2. Heavy Chain-linker- Carbiferon + Light Chain

HUMAN INTERFERON-BETA VARIANT CONJUGATED IMMUNOCYTOKINE AND METHOD FOR PREPARING SAME

CROSS-REFERENCING

This application is a continuation-in-part of International Application No. PCT/KR2016/002129, filed on Mar. 3, 2016, which claims benefit of priority to Korean Application No. KR 10-2015-0030037, filed on Mar. 3, 2015, which applications are incorporated by reference herein.

TECHNICAL FIELD

The present invention relates to an immunocytokine with a human interferon-beta variant and a method for preparing the same and, more specifically, to an immunocytokine in which an interferon-beta variant having activity and functions superior to those of natural interferon-beta is conjugated to an antibody, and to a method for preparing the same.

BACKGROUND ART

This application claims a priority from and the benefit of Korean Patent Application No. 10-2015-0030037 filed on 3 Mar. 2015, which is hereby incorporated by reference for all purposes as if fully set forth herein.

In medicines, immunotherapy represents a number of therapeutic strategies based on a concept in which an immune system is regulated to attain a preventive and/or therapeutic purpose.

Immunotherapy has been used for the treatment or prevention of various pathological conditions for years. Since cell fusion techniques have been developed to produce monoclonal antibodies, a large number of monoclonal antibodies have been produced by researchers. Thereafter, other techniques, including B cell hybridoma techniques and EBV hybridoma techniques for producing human monoclonal antibodies, have been developed for the production of monoclonal antibodies.

Monoclonal antibodies (mAb) can be developed to target almost all epitopes. Their specific recognition and conjugation properties with respect to particular cells/molecules have promoted the development of mAbs as a diagnostic and therapeutic reagent for a variety of disease conditions. Recombinant DNA techniques have been used to produce chimeric or humanized antibodies for administration to humans. Currently, several monoclonal antibodies are commercially available and used for the treatment of cancer, infectious diseases, immune diseases, and the like, while examples thereof include RITUXAN®, HERCEPTIN®, AVASTIN®, and the like.

Monoclonal antibodies are targeted molecules, and may be localized in specific regions (cells, tissues, etc.) such as pathological tissues. This characteristic has also led to the development of mAbs conjugated to a variety of materials (payloads) in an effort to target specific molecules at pathological tissue sites. These materials (payloads) may include toxins, drugs, radionuclides, prodrug compounds, and the like. Many of these conjugations involve a chemical conjugation of reactive moieties (payloads), together with specific production of antibodies and cumbersome, easily changeable procedures (U.S. Pat. No. 4,671,958).

Of these new molecules, immunocytokines are of particular interest. The immunocytokine refers to a fusion protein containing an antibody and a cytokine. Such a protein retains both antigen-binding ability and cytokine activity.

Cytokines are a category of signaling proteins and glycoproteins that, like hormones and neurotransmitters, are used extensively in cellular communication. While hormones are secreted from specific organs into the blood and neurotransmitters are related to neural activity, cytokines are a more diverse class of compounds in terms of origin and purpose. They are produced by a wide variety of hematopoietic and non-hematopoietic cell types and can have effects on both nearby cells or throughout the organism, sometimes strongly dependent on the presence of other chemicals. The cytokine family consists mainly of smaller, water-soluble proteins and glycoproteins with a mass of between 8-30 kDa. Cytokines are important in the functionalization of both natural and adaptive immune responses. Cytokines are often secreted by immune cells which have been in contact with pathogens, thereby activating and recruiting more immune cells and increasing systemic responses to pathogens.

Among cytokines, interferons (IFNs) are a kind of cytokines and have functions of exhibiting anti-viral activity, inhibiting cell proliferation, and regulating natural immune responses. Among these, interferon-beta (IFN-beta) is a spherical protein having five alpha-helices, with its size is 22 kD, and 18 kD when its glycan is removed (Arduini et al., Protein Science 8: pp 1867-1877, 1999).

Studies on the clinical application of IFN-beta are being actively conducted, and especially, IFN-beta is receiving attention as an agent for ameliorating, relieving, or treating symptoms of Multiple Sclerosis (Goodkin et al., Multiple sclerosis: Treatment options for patients with relapsing-remitting and secondary progressive multiple sclerosis, 1999).

It has been reported that, besides Multiple Sclerosis, IFN-beta shows diverse immunological activities, such as antiviral activity, cell growth inhibitory or anti-growth activity, lymphocytotoxicity-increasing activity, immunoregulatory activity, target cell differentiation-inducing or -inhibitory activity, macrophage-activating activity, cytokine production-increasing activity, cytotoxic T cell effect-increasing activity, and natural killer cell-increasing activity, and therefore, IFN-beta is effective in the treatment of cancer, auto-immune disorders, viral infections, HIV-relating diseases, hepatitis C, rheumatoid arthritis, and the like (Pilling et al., *European Journal of Immunology* 29: pp 1041-1050, 1999; Young et al., *Neurology* 51: pp 682-689, 1998; and Cirelli et al., 1995 Major therapeutic uses of interferons. *Clin Immunother* 3: pp 27-87).

Human interferon-beta is also a type of glycoprotein, and a glycan moiety linked to this protein plays an important role in the activity of the protein. Therefore, the activity of the glycoprotein may increase when a glycan is added to the glycoprotein.

Korean Patent No. 10-0781666 discloses a human interferon-beta variant having increased or improved activity or function by introducing a glycan into natural human interferon-beta, which is a glycoprotein, in view of the foregoing.

Accordingly, there is a need for the development of an immunocytokine in which, in order to use a human interferon-beta variant exhibiting efficacy superior to the pharmaceutical effect of natural interferon-beta in targeting therapy, the human interferon-beta variant is conjugated with an antibody. In addition, there is also a need for a production method for obtaining such an immunocytokine at a high yield.

DETAILED DESCRIPTION OF THE INVENTION

Technical Problem

The present inventors have invented an immunocytokine in which a human interferon-beta variant, having its increased or improved activities or functions through the introduction of a glycan into natural human interferon-beta, is conjugated with an antibody, and found that the expression level of such an immunocytokine in host cells is significantly increased compared with an immunocytokine in which natural interferon-beta is conjugated with an antibody, completing the present invention.

Therefore, an aspect of the present invention is to provide an immunocytokine comprising: (a) a human interferon-beta variant; and (b) an antibody or fragment thereof which is directly or indirectly covalently linked to the human interferon-beta variant, wherein the human interferon-beta variant is a polypeptide selected from the group consisting of (i), (ii), and (iii) below ((i) a polypeptide comprising all of the amino acid sequence disclosed in SEQ ID NO; 1; (ii) a polypeptide comprising a substantive part of the amino acid sequence disclosed in SEQ ID NO: 1; and (iii) a polypeptide substantially similar to the polypeptide of (i) or (ii)) and possesses a human interferon-beta activity, the polypeptide comprising a N-linked glycan.

Another aspect of the present invention is to provide a polynucleotide encoding the immunocytokine.

Another aspect of the present invention is to provide a method for increasing a yield of target-specific human interferon-beta, the method comprising:

(a) cloning a polynucleotide into an expression vector, the polynucleotide encoding a fusion polypeptide comprising a human interferon-beta variant, a peptide linker, and an antibody or fragment thereof;

(b) cloning the expression vector into host cells;

(c) culturing the host cells; and (d) collecting the fusion polypeptide from the cells or a culture medium, wherein the human interferon-beta variant comprises the peptide sequence selected from the group consisting of SEQ ID NO: 2 to SEQ ID NO: 4.

Another aspect of the present invention is to provide a vector including the polynucleotide.

Still another aspect of the present invention is to provide a host cell transfected with the vector.

Still further another aspect of the present invention is to provide a method for preparing an immunocytokine, the method comprising: (a) providing the host cells; (b) culturing the provided cells; and (c) preparing an immunocytokine by collecting the immunocytokine from the cells or a culture medium.

Technical Solution

In accordance with an aspect of the present invention, there is provided an immunocytokine comprising: (a) a human interferon-beta variant; and (b) an antibody or fragment thereof which is directly or indirectly covalently linked to the human interferon-beta variant, wherein the human interferon-beta variant is a polypeptide selected from the group consisting of (i), (ii), and (iii) below ((i) a polypeptide including all of the amino acid sequence disclosed in SEQ ID NO; 1; (ii) a polypeptide comprising a substantive part of the amino acid sequence disclosed in SEQ ID NO: 1; and (iii) a polypeptide substantially similar to the polypeptide of (i) or (ii)) and possesses a human interferon-beta activity, the polypeptide comprising a N-linked glycan.

In accordance with another aspect of the present invention, there is provided a method for increasing a yield of target-specific human interferon-beta, the method comprising:

(a) cloning a polynucleotide into an expression vector, the polynucleotide encoding a fusion polypeptide comprising a human interferon-beta variant, a peptide linker, and an antibody or fragment thereof;

(b) cloning the expression vector into host cells;

(c) culturing the host cells; and (d) collecting the fusion polypeptide from the cells or a culture medium, wherein the human interferon-beta variant comprises the peptide sequence selected from the group consisting of SEQ ID NO: 2 to SEQ ID NO: 4.

In accordance with another aspect of the present invention, there is provided a polynucleotide encoding the immunocytokine.

In accordance with still another aspect of the present invention, there is provided a vector comprising the polynucleotide.

In accordance with still another aspect of the present invention, there is provided a host cell transfected with the vector.

In accordance with further another aspect of the present invention, there is provided a method for preparing an immunocytokine, the method comprising: (a) providing the host cells; (b) culturing the provided cells; and (c) preparing an immunocytokine by collecting the immunocytokine from the cells or a culture medium.

Hereinafter, the present invention will be described in detail.

The therapeutic potential of cytokines is often restricted by severe side effects occurring even at their low concentrations, and as a result, sufficient concentrations of cytokines are not present in target tissues. Therefore, in order to increase the therapeutic potential of cytokines and protect normal tissues from their toxic effects, the targeting of a cytokine using an antibody and the delivery of the targeted cytokine to a disease site can be achieved by an immunocytokine.

The immunocytokine according to the present invention is a cytokine having a human interferon-beta variant with increased or improved activity or functions obtained by introducing a glycan into natural interferon-beta. The inventors completed the present invention based on the fact that when an immunocytokine in a form in which the human interferon-beta variant is conjugated with an antibody is used for target therapy for multiple sclerosis, viral diseases, and the like, such an immunocytokine might exhibit an excellent therapeutic effect compared with an immunocytokine in which a natural interferon-beta is conjugated with an antibody.

Therefore, the present invention provides an immunocytokine comprising: (a) a human interferon-beta variant; and (b) an antibody or fragment thereof which is directly or indirectly covalently linked to the human interferon-beta variant, wherein the human interferon-beta variant is a polypeptide selected from the group consisting of (i), (ii), and (iii) below ((i) a polypeptide comprising all of the amino acid sequence disclosed in SEQ ID NO: 1; (ii) a polypeptide comprising a substantive part of the amino acid sequence disclosed in SEQ ID NO: 1; and (iii) a polypeptide substantially similar to the polypeptide of (i) or (ii)) and possesses a human interferon-beta activity, the polypeptide comprising a N-linked glycan.

The human interferon-beta variant having increased or improved activity or functions compared with natural human interferon-beta is characterized in that the natural human interferon-beta or the natural human interferon-beta variant contains a glycine-asparagine-isoleucine-threonine-valine sequence at the C-terminus of the amino acid sequence thereof, and contains an N-linked glycan at the asparagine residue of the added sequence.

As used herein, the term "natural human interferon-beta variant" is meant to include all polypeptides that retain activity of human interferon-beta while having all or a part of the amino acid sequence derived from the natural human interferon-beta.

Herein, the term "activity of human interferon-beta" is defined as one or more activities sufficient for any polypeptide to be identified as human interferon-beta among activities that human interferon-beta is known to retain. Examples of such activities may include, as described above, multiple sclerosis-alleviating, -ameliorating, or -treating activity, antiviral activity, cell growth-inhibitory activity, anti-growth activity, anti-proliferative activity, lymphocytotoxicity-increasing activity, immunoregulatory activity, target cell differentiation-inducing or inhibitory activity, cytokine production-increasing activity, cytotoxic T cell effect-increasing activity, macrophage effect-increasing activity, natural killer cell-increasing activity, cancer preventing or treating activity, auto-immune disorder-preventing or -treating activity, viral infection-preventing or -treating activity, HIV-relating disease-preventing or -treating activity, hepatitis C-preventing or -treating activity, rheumatoid arthritis-preventing or -treating activity, and the like.

Herein, the term "polypeptide comprising all or a part of the amino acid sequence derived from natural human interferon-beta" is meant to include a polypeptide comprising all or a substantive part of the amino acid sequence of SEQ ID NO: 1, which is an amino acid sequence of natural human interferon-beta, or a polypeptide substantially similar to such a polypeptide.

Here, the term "polypeptide comprising a substantive part of all of the amino acid sequence of SEQ ID NO: 1" is defined as a polypeptide comprising a part of the amino acid sequence of SEQ ID NO: 1, the polypeptide having the activity equal to or higher than the activity of natural human interferon-beta having the amino acid sequence of SEQ ID NO: 1, or still retaining the activity of human interferon-beta even if its activity is low. Further, the term "polypeptide substantially similar to all or a substantive part of the amino acid sequence of SEQ ID NO: 1" is defined as a polypeptide comprising all or a substantive part of the amino acid sequence of SEQ ID NO: 1, the polypeptide having the activity equal to or higher than the activity of natural human interferon-beta having the amino acid sequence of SEQ ID NO: 1, or still retaining the activity of human interferon-beta even if its activity is low.

The polypeptide comprising a substantive part of all of the amino acid sequence of SEQ ID NO: 1 may be a polypeptide in which a N-terminus region and/or a C-terminus region is deleted from the polypeptide comprising the amino acid sequence of SEQ ID NO: 1. The polypeptide substantially similar to all or a substantive part of the amino acid sequence of SEQ ID NO: 1 may be a polypeptide in which an amino acid prior to substitution is chemically equivalent to a substituted amino acid even though at least one amino acid is substituted, for example, alanine as a hydrophobic amino acid is substituted with another hydrophobic amino acid, especially a more hydrophobic amino acid, such as valine, leucine, or isoleucine.

In some cases, a polypeptide in which a N-terminus region and/or a C-terminus region is deleted or a polypeptide comprising a substituted amino acid may not exhibit the activity of human interferon-beta since the N-terminus region, C-terminus region, or substituted amino acid is involved in an essential motif in the activity of human interferon-beta. Nonetheless, the distinction and detection of such inactive polypeptides from active polypeptides, through the verification of whether the above polypeptide derived from SEQ ID NO: 1 has one or more activities as described above, and/or through a method associated with the identification of human interferon-beta known in the art at the filing date of the present application, fall within the understanding of an ordinary skilled person in the art.

Therefore, the human interferon-beta variant according to the present invention may be defined as one of the following peptides which retain human interferon-beta activity while containing a glycine-asparagine-isoleucine-threonine-valine sequence at the C-terminus and an N-linked glycan at that position, or as one of the polypeptides in which at the 27th amino acid residue of the wild-type interferon-beta, arginine (R27) is altered with threonine (R27T) or serine (R27S):

(a) a polypeptide comprising all of the amino acid sequence disclosed in SEQ ID NO; 1;

(b) a polypeptide comprising a substantive part of the amino acid sequence disclosed in SEQ ID NO: 1; and (c) a polypeptide substantially similar to the polypeptide of (a) or (b). More preferably, the human interferon-beta variant refers to a polypeptide comprising the amino acid sequence of any one of SEQ ID NO: 2 to SEQ ID NO: 4.

Therefore, it should be understood that the human interferon-beta variant according to the present invention includes all the polypeptides that retain human interferon-beta activity while containing a glycine-asparagine-isoleucine-threonine-valine sequence at the C-terminus and containing a N-linked glycan at that position.

As described above, the human interferon-beta variant according to the present invention is meant to include all the polypeptides that retain human interferon-beta activity while containing a glycine-asparagine-isoleucine-threonine-valine sequence at the C-terminus and containing a N-linked glycan at that position.

More preferably, the "human interferon-beta variant" of the present invention may be an interferon-beta mutein having the amino acid sequence of any one of SEQ ID NO: 2 to SEQ ID NO: 4, and has been named "Carbiferon" by the present inventors. The Carbiferon of the present invention is a type in which one or two glycans are added to natural interferon-beta. More preferably, the Carbiferon according to the present invention means a polypeptide in which the 27th amino acid arginine (R) is substituted with threonine (T) or serine (S) in natural human interferon-beta having the amino acid sequence of SEQ ID NO: 1 or a polypeptide which contains a glycine-asparagine-isoleucine-threonine-valine (G-N-I-T-V) sequence at the C-terminus of natural human interferon-beta and a N-linked glycan at that position.

The human interferon-beta variant shows improved or increased antiviral activity, cell growth-inhibitory activity, immunoregulatory functions, and in-vivo half-life, compared with natural interferon-beta.

SEQ ID NO: 2 is the amino acid sequence of interferon-beta variant R27T, and SEQ ID NO: 3 is the amino acid sequence of interferon-beta variant R27S in which the 27th amino acid is substituted with S in SEQ ID NO: 1. In addition, SEQ ID NO: 4 is the amino acid sequence of interferon-beta variant GNITV in which GNITV amino acids are contained after the termination codon. SEQ ID NOs: 1 to 4 contain an initiation codon at the N-terminus, and when the proteins of SEQ ID NOs: 1 to 4 are linked to another linker (the C-terminus of the linker being linked to the N-terminus of Carbiferon), the initiation codon may be omitted. That is, the nucleotide sequence ATG or the amino acid sequence methionine of the initiation codon of the proteins of SEQ ID NOs: 1 to 4 may be omitted.

Meanwhile, the "human interferon-beta variant" is described in detail in Korean Patent No. 10-0781666.

As used herein, the antibodies may vary widely, and include monoclonal antibodies, polyclonal antibodies, multi-specific antibodies (e.g., bi-specific antibodies) and antibody fragments (as long as they exhibit desired antigen-binding activity), while including various antibody structures without limitation thereto. Natural antibodies are molecules with various structures. For example, natural IgG antibody is a tetrameric glycoprotein with about 150,000 daltons, composed of two identical light chains and two identical heavy chains which are disulfide-linked. From the N-terminus to the C-terminus, each heavy chain has a variable domain (VH), also called a variable heavy chain domain or a heavy chain variable domain, followed by three or four constant domains (CH1 CH2, CH3 and optionally CH4). Similarly, from the N-terminus to the C-terminus, each light chain has a variable domain (VL), also called a variable light chain domain or a light chain variable domain, followed by a constant light chain (CL) domain. The light chain of an antibody may be assigned to one of two types, called kappa (κ) and lambda (k), based on the amino acid sequence of the constant domain thereof.

The antibody of the present invention may be a human antibody, a chimeric antibody, and/or a humanized antibody, but is not limited thereto.

The chimeric antibody includes an antibody composed of a variable region of murine immunoglobulin and a constant region of human immunoglobulin. Such an alteration is simply configured such that a murine antibody constant region is substituted with a human constant region, thereby producing a human/murine chimera capable of having a sufficiently low immunogenicity so as to allow for its pharmaceutical usage.

The term "humanized antibody" means an antibody (wholly or partially) composed of an amino acid sequence derived from the human antibody germline by modifying the sequence of an antibody having a non-human complementarity-determining region (CDR). The humanization of antibody variable region and CDR is conducted by a technique well known in the art. Such an antibody is needed for Fc-dependent effector function, but retains a human constant region, which is significantly less likely to induce an immune response to the antibody. As an example, the framework regions of the variable regions are substituted with corresponding human framework regions that leave non-human CDR substantially intact, or even replace CDR with sequences derived from the human genome (See e.g. Patent application US 2006/25885). Fully human antibodies are produced in genetically modified mice of which immune systems have been altered to correspond to human immune systems. A humanized antibody also refers to an antibody encompassing a human framework, at least one CDR from a non-human antibody, wherein any constant region present is substantially identical to a human immunoglobulin constant region, i.e., at least about 85% or 90%, and preferably at least 95% identical. Hence, all of the humanized antibody (except for possibly CDRs) are substantially identical to corresponding parts of at least one natural human immunoglobulin sequence.

The term "antibody fragment" as used herein refers to an antibody fragment capable of responding to the same antigen as its antibody counterpart. Such fragments can be simply identified by a person skilled in the art, and for example, may include $F_{ab}$ fragment (e.g., by papain digestion), $F_{ab}'$ fragment (e.g., by pepsin digestion and partial reduction), $F(_{ab}')_2$ fragment (e.g., by pepsin digestion), $F_{acb}$ (e.g., by plasmin digestion), $F_d$ (e.g., by pepsin digestion, partial reduction, and re-aggregation), and $scF_v$ (single chain Fv; e.g., by molecular biology techniques) fragment. Such fragments can be produced by enzymatic cleavage, synthetic, or recombinant techniques, as known in the art and/or as described herein.

It was verified that an immunocytokine with a human interferon-beta variant according to the present invention showed interferon-beta activity by inducing cytotoxicity and pSTAT-1 phosphorylation, which were not shown in an antibody per se (see examples 3 and 4).

The present invention provides an immunocytokine characterized in that the antibody or fragment thereof is an antibody or fragment thereof to an antigen selected from the group consisting of tumor antigens and multiple sclerosis-specific antigens.

Tumors growing to a predetermined size or larger need to form new blood vessels in order to further grow or migrate into other sites. Therefore, the molecules and signaling systems involved in the formation of new blood vessels may be important therapeutic targets in an anticancer therapy. Meanwhile, interferon-beta has been reported to inhibit the growth of tumor cells by inhibiting the angiogenesis of tumor cells. In addition, interferon-beta may induce tumor cell death to exhibit an anti-cancer effect by inducing an innate or acquired immune response in the environment surrounding a tumor site.

Therefore, the human interferon-beta variant according to the present invention has improved activity and functions compared with natural interferon-beta, so that when used for target therapy for a cancer patient, a form of an immunocytokine, in which the human interferon-beta variant is conjugated with an antibody specifically recognizing a tumor antigen, will exhibit superior therapeutic effects compared with an immunocytokine in which natural interferon-beta is conjugated with the antibody.

The tumor antigen is a protein that is produced by tumor cells inducing an immune response, especially, a T cell-mediated immune response. Tumor antigens are well known in the art, and examples thereof include a glioma-associated antigen, carcinoembryonic antigen (CEA), β-human chorionic gonadotropin, alpha-fetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-Iα, p53, prostein, PSMA, Her2/neu, survivin and telomerase, prostate-carcinoma tumor antigen-1 (PCTA-1), MAGE, ELF2M, neutrophil elastase, ephrin-B2, CD22, insulin growth factor (IGF)-I, IGF-II, IGF-I receptor, or mesothelin.

The type of tumor antigen designated herein may also be a tumor-specific antigen (TSA) or a tumor-associated antigen (TAA). TSA is unique to tumor cells, and does not present on other cells in the body. TAA is not unique to tumor cells, and, instead, is also expressed in normal cells under conditions that fail to induce a state of immunologic tolerance to the antigen. The expression of the antigen to a tumor may occur under conditions in which an immune system responds to the antigen. TAA may be an antigen that is expressed on normal cells during fetal development when the immune system is immature and unable to respond, or may be an antigen that is normally present at an extremely low level on normal cells, while being expressed at a higher level on tumor cells.

Non-limiting examples of TSA or TAA include: differentiation antigens, such as MART-1/MelanA (MART-I), gplOO (Pmel 17), tyrosinase, TRP-1, and TRP-2; tumor-specific multilineage antigens, such as MAGE-1, MAGE-3, BAGE, GAGE-1, GAGE-2, and p15; overexpressed embryonic antigens, such as CEA; overexpressed oncogenes, and mutated tumor-suppressor genes, such as p53, Ras, HER-2/neu; unique tumor antigens resulting from chromosomal translocations, such as BCR-ABL, E2A-PRL, H4-RET, IGH-IGK, MYL-RAR; and viral antigens, such as Epstein Barr virus antigens EBVA and human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, β-Catenin, CDK4, Mum-1, p 15, p 16, 43-9F, 5T4, 791Tgp72, α-fetoprotein, β-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

The antibodies specifically recognizing the tumor antigens include, for example, HuM195 (see, e.g., Kossman et. al, (1999) Clin. Cancer Res. 5: 2748-2755), CMA-676 (see, e.g., Sievers et. al, (1999) Blood 93: 3678-3684), AT13/5 (see, e.g., Ellis et. al, (1995) J. Immunol. 155: 925-937), HB7, trastuzumab (see, e.g., HERCEPTIN; Fornier et. al., (1999) Oncology (Huntingt) 13: 647-58), TAB-250 (Rosenblum et. al., (1999) Clin. Cancer Res. 5: 865-874), BACH-250 (Id.), TA1 (Maier et. al., (1991) Cancer Res. 51: 5361-5369), mAb disclosed in U.S. Pat. Nos. 5,772,997 and 5,770,195 (mAb 4D5; ATCC CRL10463); and mAb disclosed in U.S. Pat. No. 5,677,171, Mc5 (see, e.g., Peterson et. al., (1997) Cancer Res. 57: 1103-1108; Ozzello et. al., (1993) Breast Cancer Res. Treat. 25: 265-276), hCTMO1 (see, e.g., Van Y M et. al., (1996) Cancer Res. 56: 5179-5185) CC49 (see, e.g., Pavlinkova et. al., (1999) Clin. Cancer Res. 5: 2613-2619), B72.3 (see, e.g., Divgi et. al., (1994) Nucl. Med. Biol. 21: 9-15), mouse monoclonal anti-HM1.24 IgG2a/κ, humanized anti-HM1.24 IgG1/κ antibody (see, e.g., Ono et. al., (1999) Mol. Immuno. 36: 387-395), trastuzumab (see, e.g., HERCEPTIN, Fornier et. al., (1999) Oncology (Huntington) 13: 647-658), TAB-250 (Rosenblum et. al., (1999) Clin. Cancer Res. 5: 865-874), BACH-250 (Id.), TA1 (see, e.g., Maier et. al., (1991) Cancer Res. 51: 5361-5369), rituximab, ibritumomabtiuxetan, and tositumomab, AME-133v (Applied Molecular Evolution), ocrelizumab (Roche), ofatumumab (Genmab), TRU-015 (Trubion), IMMU-106 (Immunomedics), and the like, but are not limited thereto.

The present invention is not necessarily limited to the use of the antibodies described above, and such other antibodies as those known to those skilled in the art may be used in the compositions and methods described herein.

Meanwhile, IFN-beta was first introduced as a therapeutic agent for Multiple Sclerosis to obtain an antiviral effect, and thereafter, the mechanisms thereof have been revealed through many studies. First, IFN-beta inhibits the activation of HLA class II molecules induced by IFN-α, thereby inhibiting antigen expression and preventing T-cell activation. In addition, IFN-beta inhibits T-cell activation by inactivating co-stimulatory molecules, and induces the apoptosis of auto-responsive T cells. With respect to the effects of IFN-beta on the brain-blood barrier, IFN-beta is believed to inhibit the adherence of T cells to vascular endothelial cells and to reduce their ability to enter the brain. In this regard, MRI studies have reported that contrast enhancement lesions were reduced in about 90% of multiple sclerosis patients receiving IFN-beta treatment.

Therefore, the human interferon-beta variant according to the present invention has improved activity and functions compared with natural interferon-beta, so that when used for target therapy, a form of an immunocytokine in which the human interferon-beta variant is conjugated with an antibody recognizing a multiple sclerosis-specific antigen will exhibit therapeutic effects superior to those of an interferon-beta agent alone.

Examples of the multiple sclerosis-specific antigen and antibody include CD20 and Rituximab as an antibody recognizing the same, CD52 and alemtuzumab as an antibody recognizing the same, and an interleukin-2a receptor and daclizumab recognizing the same, but are not limited thereto.

The present invention also provides an immunocytokine in which the human interferon-beta variant is conjugated to the antibody or a fragment thereof via a peptide linker. A peptide linker refers to a short-fragment amino acid or amino acid analogue in which two or more amino acids or amino acid-like substances are linked to each other by peptide linkages, and serves to link two or more separate substances to each other. A glycine-serine linker, a glycine-serine-alanine linker, or the like may be prepared by using amino acids such as glycine, serine, and alanine as a main constituent. According to a preferable embodiment of the present invention, the linker may be composed of or contain the amino acid sequence of any one of SEQ ID NO: 5 to SEQ ID NO: 11.

The immunocytokine of the invention may preferably contain a flexible linker sequence inserted between the human interferon-beta variant and a polypeptide of an antibody or fragment thereof. The linker sequence allows effective positioning of the antibody or fragment thereof with respect to the human interferon-beta variant, thereby allowing activity of both domains.

The linker refers to a naturally derived peptide linker or a synthetically derived peptide linker. The peptide linker consists of a linear amino acid chain, wherein 20 types of naturally occurring amino acids are monomeric building blocks. The linker may have a repetitive amino acid sequence or may have a naturally occurring polypeptide, for example, a polypeptide sequence having a hinge function. All peptide linkers may be encoded by nucleic acid molecules, and thus may be expressed in a recombinant manner. Since a linker per se is a peptide, a human interferon-beta variant and an antibody or fragment thereof are linked to the linker through a peptide linkage.

A linker is composed of amino acids linked together via peptide linkages, preferably 1 to 20 amino acids linked by a peptide linkage, wherein the amino acids are selected among 20 natural amino acids. Of these amino acids, at least one is glycosylated as understood by a person skilled in the art. Preferably, the 1 to 20 amino acids are selected from glycine, alanine, proline, asparagine, glutamine, and lysine, but are not limited thereto.

Suitable linkers include, for example, a cleavable linker and a non-cleavable linker. Typically, a cleavable linker is easily cleaved under intracellular conditions. A suitable cleavable linker includes, for example, a peptide linker that is cleavable by intracellular protease, such as lysosomal proteases or endosomal proteases.

With respect to the linker, for example, the N-terminus of the linker may be linked to the heavy chain C-terminus of the antibody. The linkage of the linker to the heavy chain C-terminus of the antibody is preferably conducted in a manner in which a nucleotide sequence encoding a linker sequence is linked to an expression vector expressing the antibody of the present invention while the protein expression frames are matched so that the nucleotide sequence is directly linked to the antibody expressed by the expression vector. In addition, the linker may be linked to the light chain C-terminus of the antibody, or may be linked to each of the light chain C-terminus and the heavy chain C-terminus of the antibody. In addition, the N terminus of the interferon-beta variant of the present invention is linked to the C-terminus of the linker.

The peptide linker of the present invention may be a peptide linker known in the art, but may preferably be a glycine-serine linker or a peptide linker containing an amino acid sequence of SEQ ID NO: 5 to SEQ ID NO: 11.

Preferably, the peptide linker may be a gly-ser linker, for example, $(Gly_xSer_y)_z$ type (wherein x is an integer of 1 to 5, y is an integer of 1 to 2, and z is an integer of 1 to 6), such as $(gly_4ser_1)_3$ or $(gly_3ser_2)_3$, and more preferably may be a linker represented by the amino acid sequence of GGGGS or GGGGSGGGGSGGGSG, but is not limited thereto.

In addition, the present invention provides an immunocytokine characterized in that the amino acid sequence of the human interferon-beta variant polypeptide is located at a heavy chain C-terminus, a light chain C-terminus, or each of heavy and light chain C-termini of the amino acid sequence of the antibody or fragment thereof.

The amino acid sequence of the human interferon-beta variant may be located at a heavy chain C-terminus, a light chain C-terminus, or each of heavy and light chain C-termini of the amino acid sequence of the antibody or fragment thereof, and may be preferably located at the C-terminus of the amino acid sequence of the antibody or fragment thereof.

The present invention also provides an immunocytokine characterized in that the immunocytokine comprises an amino acid sequence selected from the group consisting of SEQ ID NO: 12, 13, 15, and 17.

The present invention provides an immunocytokine, comprising: (a) a human interferon-beta variant represented by any one of SEQ ID NO: 2 to SEQ ID NO: 4; (b) a peptide linker represented by any one of SEQ ID NO: 5 to SEQ ID NO: 11; and (c) an antibody or fragment thereof.

The present invention also provides a polynucleotide encoding the immunocytokine.

The polypeptide as described above may be used without limitation as long as the polypeptide encodes the peptide of the immunocytokine of the present invention, in which a human interferon-beta variant is conjugated with an antibody or fragment thereof, and may include all of DNA, cDNA, and RNA sequences. Preferably, the polynucleotide refers to a substance which has the amino acid sequence represented by SEQ ID NO: 3 or an amino acid sequence having at least 70% homology with the amino acid sequence, while it may be isolated from nature or may be prepared by a genetic engineering method that is well-known in the art.

The present invention provides a vector comprising the polynucleotide.

The vector refers to an expression vector which is prepared so as to express the immunocytokine of the present invention by inserting the polynucleotide according to the present invention into a vector by any method well known in the art through appropriate transcription/translation regulator sequences.

The polynucleotide sequence cloned according to the present invention may be operably linked to an appropriate expression control sequence, while the operably linked gene sequence and the expression control sequence may be contained in one expression vector having both a selection marker and a replication origin. The term "operably linked" means that the polynucleotide sequence is linked to the expression control sequence in a manner of allowing its gene expression. The term "expression control sequence" refers to a DNA sequence which controls the expression of an operably linked polynucleotide sequence in a particular host cell. Such an expression control sequence may include at least one selected from the group consisting of a promoter for performing transcription, an operator sequence for controlling transcription, a sequence for encoding a suitable mRNA ribosomal binding site, and a sequence for controlling the termination of transcription and translation.

The vector used as a parent vector of the expression vector is not particularly limited, while any plasmid, virus, or other medium, which is commonly used for expression in a microorganism used as a host cell in a technical field to which the present invention pertains, can be used. Examples of the plasmid may include *Escherichia coli*-derived plasmids (pBR322, pBR325, pUC118, pUC119, and pET-22b (+)), *Bacillus subtilis*-derived plasmids (pUB110 and pTP5), and yeast-derived plasmids (YEp13, YEp24, and YCp50), but are not limited thereto. Examples of the virus may include animal viruses (such as retrovirus, adenovirus, and vaccinia virus), insect viruses (such as baculovirus), and the like, but are not limited thereto.

The present invention provides host cells transfected with the vector.

The host cells may be selected from ones that control the expression of an inserted sequence or allow genetic products to proceed in a preferable specific manner. Different host cells have their own characteristic and specific mechanisms in terms of protein translation, post-translational processing and modification. A suitable cell line or host system may be selected from ones that provide preferable modification and processing of expressed heterologous proteins. The expression in yeasts can produce biologically active products. The expression in eukaryotic cells can increase the likelihood of "natural" folding.

Any host cell known in the art may be used as a host cell capable of performing its continuous cloning and expression while stabilizing the vector according to the present invention. Examples of the host cells may include *E. coli* JM109, *E. coli* BL21DE, *E. coli* DH5, *E. coli* RR1, *E. coli* LE392, *E. coli* B, *E. coli* X 1776, and *E. coli* W3110. Also, *Agrobacterium* spp. strains such as *Agrobacterium* A4, *Bacilli* spp. strains such as *Bacillus subtilis*, other intestinal bacteria such as *Salmonella typhimurium* or *Serratia marcescens*, and various *Pseudomonas* spp. strains may be used as host cells.

In addition, in cases where eukaryotic cells are transfected with the vector according to the present invention, yeast (*Saccharomyces cerevisiae*), insect cells and human cells (e.g., CHO cell line (Chinese hamster ovary), W138, BHK, COS-7, 293, HepG2, 3T3, RIN, and MDCK cell lines) may be used as a host cell.

The host cell herein may preferably be a CHO cell line.

Any known method in which host cells are transfected with a vector delivered thereinto may be used, but is not particularly limited. For example, the host cells may be transfected by calcium phosphate precipitation, a DEAE-dextran method, electroporation, direct microinjection, a DNA-loaded liposome method, a lipofectamine-DNA complex method, cell sonication, gene bombardment using high-velocity microprojectiles, a polycation method, and receptor-mediated transfection. Some of these techniques may be modified for use in vivo or ex vivo.

The present invention provides a method for preparing an immunocytokine, the method comprising: (a) providing host cells; (b) culturing the provided cells; and (c) preparing an immunocytokine by collecting the immunocytokine from the cells or a culture medium.

Transgenic microorganisms are cultured under suitable conditions allowing the expression of, as a target protein, an immunocytokine in which a human-beta variant is conjugated to an antibody or fragment thereof, and such conditions may be established by a method well known to a person skilled in the art. Transgenic microorganisms may be cultured in large quantities by a routine culturing method. A medium containing carbon sources, nitrogen sources, vitamins, and minerals may be used as a culture medium, and for example, Luria-Bertani broth (LB medium) may be used. The microorganisms may be cultured under conventional microorganism culture conditions, and, for example, may be cultured at a temperature range of 15-45° C. for 10-40 hours. Centrifugation or filtration may be carried out to remove the culture medium in the culture fluid and to recover only concentrated cells, and these steps may be carried out as needed by a person skilled in the art. The concentrated cells are frozen or lyophilized by a routine method, so that the cells can be preserved so as not to lose the activity thereof.

The proteins expressed in transgenic microorganisms (or transformants) may be purified in a conventional manner. For instance, the immunocytokine according to the present invention may be purified by using salting out (e.g., ammonium sulfate precipitation or sodium phosphate precipitation), solvent precipitation (e.g., protein fraction precipitation using acetone, ethanol, and the like), dialysis, gel filtration, ion exchange, column chromatography such as reverse column chromatography, and ultra-filtration, alone or in combination (Maniatis et al, Molecular Cloning: A Laboratory Manual, Cold Spring Harbor Laboratory, Cold Spring Harbor, N.Y. (1982); Sambrook et al, Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

The immunocytokines with human interferon-beta variants according to the present invention can be produced at a remarkably excellent efficiency, compared with immunocytokines with human interferon-beta (See Example 2).

Meanwhile, the present invention provides a method for increasing a yield of target-specific human interferon-beta, the method comprising:

(a) cloning a polynucleotide into an expression vector, the polynucleotide encoding a fusion polypeptide comprising a human interferon-beta variant, a peptide linker, and an antibody or fragment thereof;

(b) cloning the expression vector into host cells;

(c) culturing the host cells; and (d) collecting the fusion polypeptide from the cells or a culture medium, wherein the human interferon-beta variant comprises the peptide sequence selected from the group consisting of SEQ ID NO: 1 to SEQ ID NO: 4.

Each element for the yield increasing method of the present invention is as described above, while the target-specific human interferon-beta may be the immunocytokine according to the present invention.

Advantageous Effects

The immunocytokines containing human interferon-beta variants and antibodies or fragments thereof according to the present invention exhibit both activity of interferon-beta and characteristics of the antibodies, and thus can be used for targeting therapy for Multiple Sclerosis or cancer. The immunocytokines according to the present invention may be prepared at an excellent efficiency, compared with immunocytokines with natural interferon-beta.

MODE FOR CARRYING OUT THE INVENTION

Hereinafter, the present invention will be described in detail.

However, the following Examples are merely for illustrating the present invention and are not intended to limit the scope of the present invention.

Example 1

Vector Cloning and Host Cell Transfection

For the cloning of an immunocytokine in which an interferon-beta variant is conjugated with an antibody heavy chain (ACC #2) and an immunocytokine in which an interferon-beta variant is conjugated with an antibody light chain (ACC #7), B12 sequence was used. The human interferon-beta variant sequences were inserted into the heavy chain and light chain of the B12 sequence using a linker, respectively, followed by synthesis using a vector. The synthesized genes were digested with respective proper restriction enzymes, and ligated to the IgG expression vector, followed by a sequencing process, thereby finally constructing vectors expressing ACC #2 and ACC #7. upon completion of the cloning, the ACC #2 and ACC #7 vectors were respectively extracted in large quantities through transformation, and then used for transfection.

CHO-S cells were subcultured for at least 5 passages at a density of $3 \times 10^5$ cells/ml to be prepared for transfection. When the survival rate of the cells was maintained at 90% or higher after the subculture, the cells were seeded at a density of $5 \times 10^5$ cells/mL to be prepared for transfection. The survival rate (>95%) and cell density ($1 \times 10^6$ cells/mL) were monitored at 24 h after the cell seeding, and 50 μg of DNA was transfected into CHO-S cells, which were cultured in a 30-mL culture medium, using a transfection solvent.

Example 2

Confirmation of Immunocytokine Expression in Host Cells 48 hours after cell transfection, the expression levels of ACC #2 and ACC #7 were determined by concentration measurement (BCA assay) and western-blot assay.

For BCA assay, reagent A (containing sodium carbonate, bicinchoninic acid, and the like) and reagent B (containing 4% cupric sulfate) were prepared at a ratio of 50:1, and mixed with the standard solution (BSA solution, 0-2000 ug/ml) and a sample (10 uL of sample and 200 uL of reagent). The resultant solution was incubated at 37° C. for 30 minutes, and then the absorbance was determined at 562 nm for concentration calculation. The curve obtained based on the standard solution was used for the concentration calculation.

Western-blot testing was conducted as described below. First, each of the cultured media was collected, and loaded on 10% SDS PAGE gel. The loaded gel was transferred onto PVDF membrane, which was then blocked with 5% BSA solution, and then probed with primary and secondary antibodies. After completion of washing with TBST solution, the membrane was imaged on a film. The image of the film was developed with developer and fixer.

Figure 1:
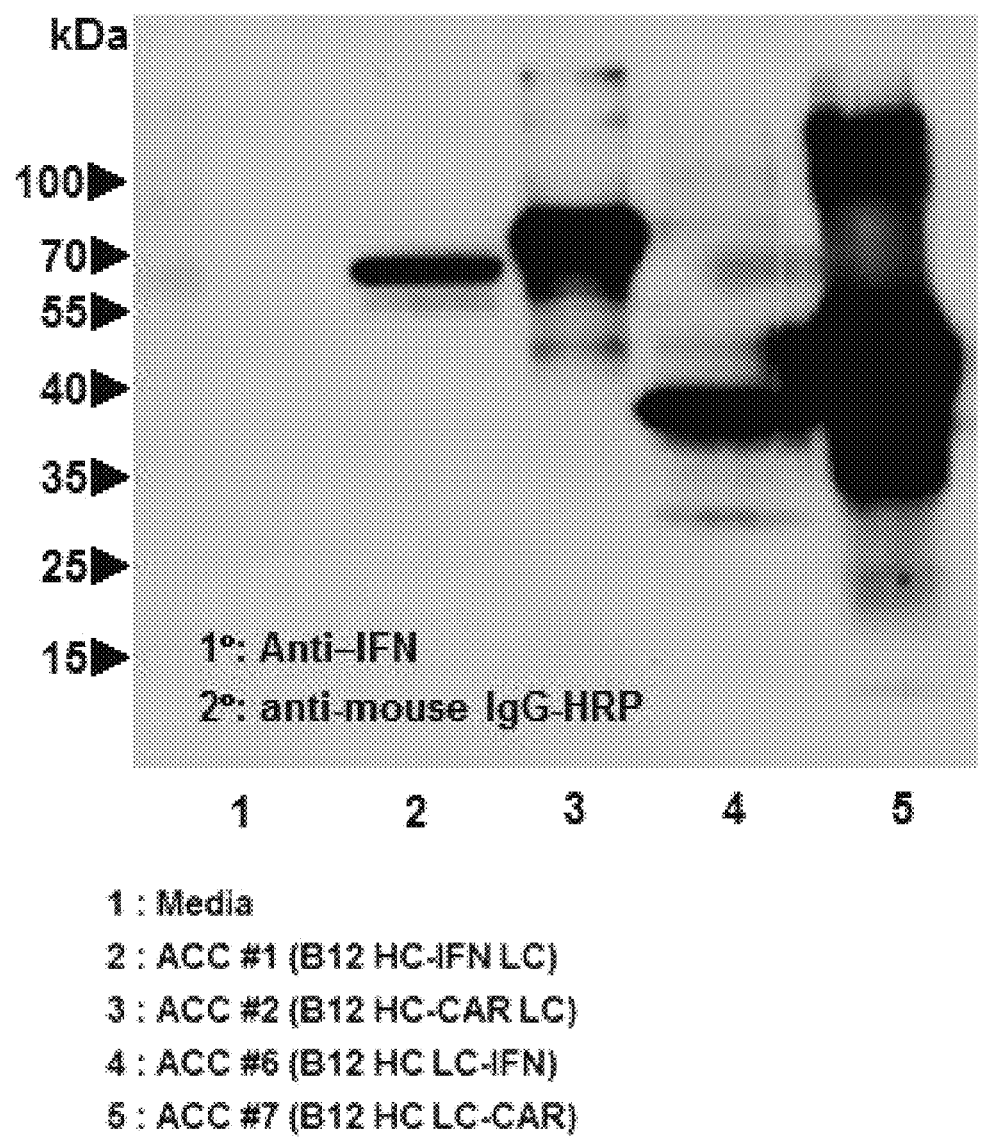
FIG. 1 shows the results of western blot analysis of the expression levels of the immunocytokines produced in host cells according to the present invention (1: culture medium, 2: B12 heavy chain-natural interferon, 3: B12 heavy chain-interferon variant, 4: B12 light chain-natural interferon, 5: B12 light chain-interferon variant).

The results indicated that the expression levels of the immunocytokines in which the human interferon-beta variants were conjugated to B12 heavy and light chains were higher than those of the immunocytokine in which the natural human interferons were conjugated to B12 heavy and light chain (FIG. 1).

Example 3

Preparation of Immunocytokines

Figure 2:
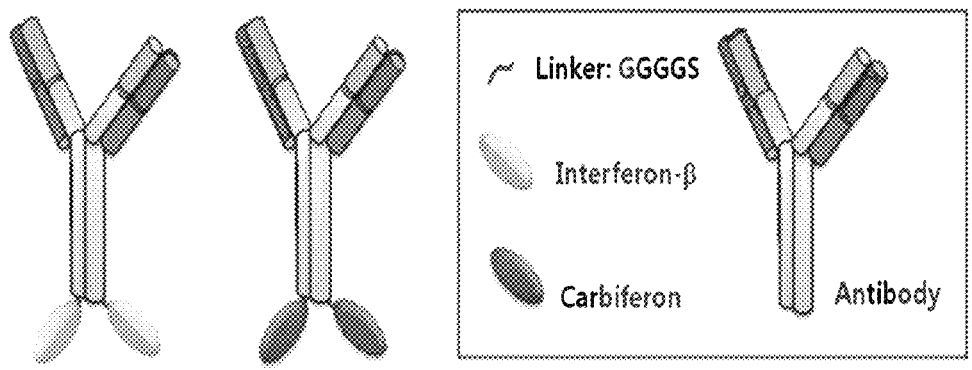
FIG. 2 is a schematic diagram showing the immunocytokine with the human interferon-beta variant according to the present invention.

The linker represented by SEQ ID NO: 5 was inserted into a heavy chain region of an antibody, and interferon-beta or an interferon-beta variant was conjugated thereto. FIG. 2 is a schematic diagram showing a structure of an immunocytokine with a human interferon-beta variant.

Figure 3:
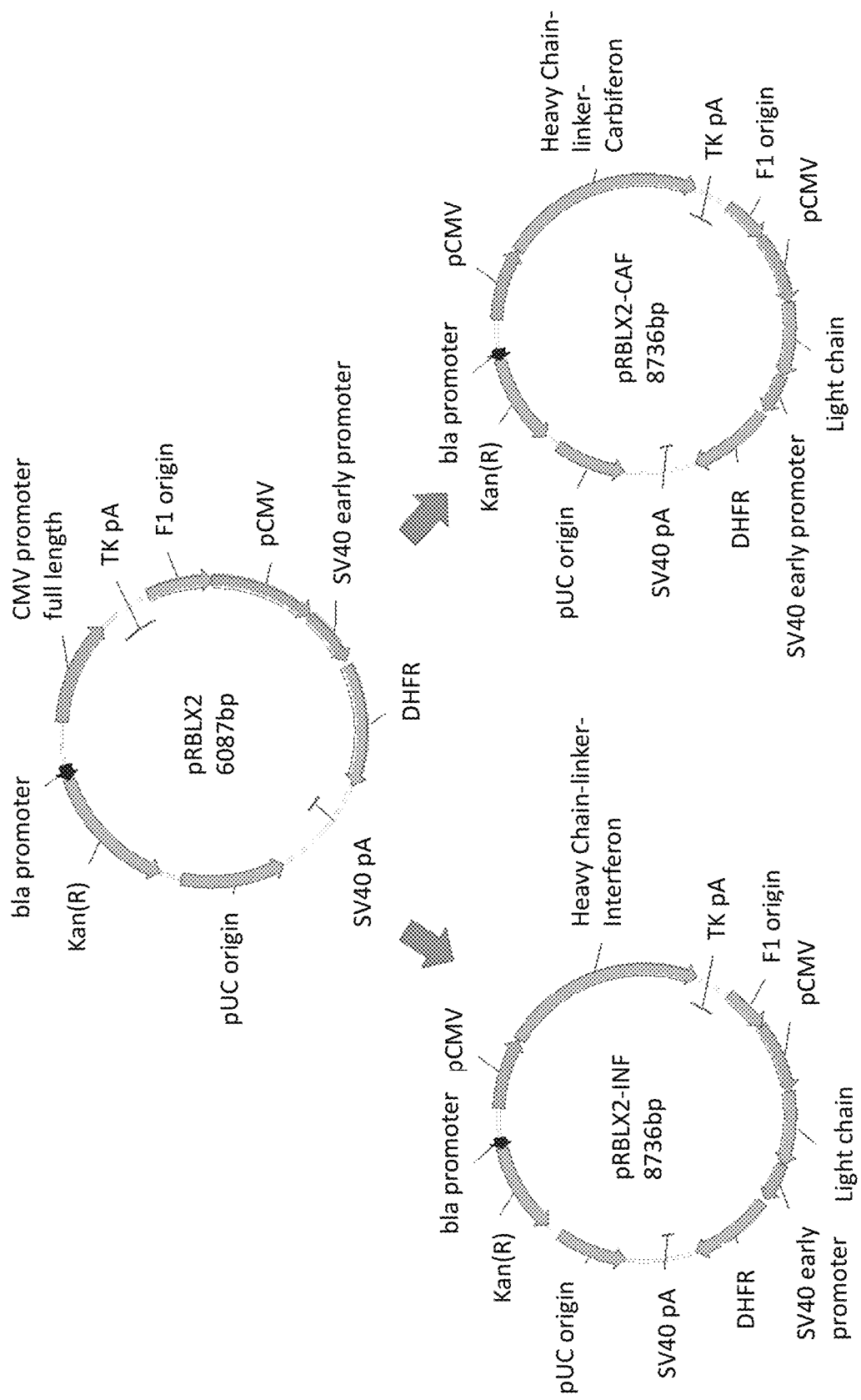
FIG. 3 is a schematic diagram showing a procedure of constructing pRBLX2-INF by inserting a gene nucleotide sequence of heavy chain-linker-interferon into pRBLX2 vector (left) and a procedure of constructing pRBLX2-CAF by inserting a gene nucleotide sequence of heavy chain-linker-interferon-beta variant into pRBLX2 vector (right).

The linker represented by SEQ ID NO: 5 and interferon-beta or interferon-beta variant were cloned into a heavy chain of an antibody. Thereafter, restriction enzymes AvrII (CCTAGG) cleavage site and Bstz17I (GTATAC) cleavage site were inserted into the 3'-terminus and the 5'-terminus of the whole gene, respectively, thereby ensuring a final gene of the heavy chain. In addition, restriction enzymes EcoRV (GATATC) cleavage site and Pad (TTAATTAA) cleavage site were inserted into the 3'-terminus and the 5'-terminus of a light chain of the antibody, respectively, thereby ensuring a final gene of the light chain. FIG. 3 shows a schematic diagram of the production procedures.

Example 4

Confirmation of Immunocytokine Expression

For confirmation of the expression of an immunocytokine with human interferon-beta and an immunocytokine with a human interferon-beta variant, 50 μg of pRBLX2-INF or pRBLX2-CAF vector was transfected into CHO-S cells, and the expression was induced while the cells were cultured for 7 days. After 7 days, the culture liquid was collected, and then centrifuged (8000 rpm, 10 minutes) to remove cells. A small amount of the culture liquid with cells removed was taken, mixed with 5× sample buffer, and boiled at 100 □ for 10 minutes, thereby inducing sufficient protein denaturation. The prepared sample was loaded onto a Tricine SDS-PAGE gel together with a marker, and subjected to electrophoresis at a voltage of 130 V for 1 hour and 30 minutes. Thereafter, the gel was carefully separated, immersed in a Coomassie blue staining solution, and then shaken for 30 minutes for staining. After the staining, the gel was transferred into a de-staining buffer, and then de-stained with shaking for 30 minutes. The de-staining was repeated three times.

For clearer comparison of the expression levels, western blotting was performed using anti-interferon-beta antibody and anti-human IgG-HRP. After Tricine SDS-PAGE was performed by the same method as above, the gel was carefully separated, and placed on 3M paper, and then a polyvinylidene difluoride (PVDF) membrane was disposed thereon, and again covered with 3M paper. Thereafter, the resultant structure was immersed in 1× transfer buffer and proteins were transferred at a voltage of 100 V for 70 minutes. The membrane was blocked at room temperature for 1 hour and 30 minutes by adding 5% Tris-buffered saline-Tween 20 (TBS-T, 0.1% Tween 20). The PVDF membrane was washed twice with TBS-T, and then immersed in TBS-T. The anti-interferon-beta antibody was prepared by dilution in TBS-T at 1:1000, while the anti-human IgG-HRP antibody was prepared by dilution in TBS-T at 1:3000. The membrane was immersed in the antibody dilution, followed by reaction at room temperature for 2 hours with shaking. After the completion of this procedure, the resulting product was washed three times with TBS-T for 10 minutes, and then allowed to react at room temperature for 1 hour by adding a secondary antibody conjugated with horseradish peroxidase (HRP). After washing was again conducted, bands were identified using an enhanced chemiluminescence (ECL, Intron) reagent. The intensities of the bands were determined by using C-DiGit (LI-COR, USA).

Figure 4:
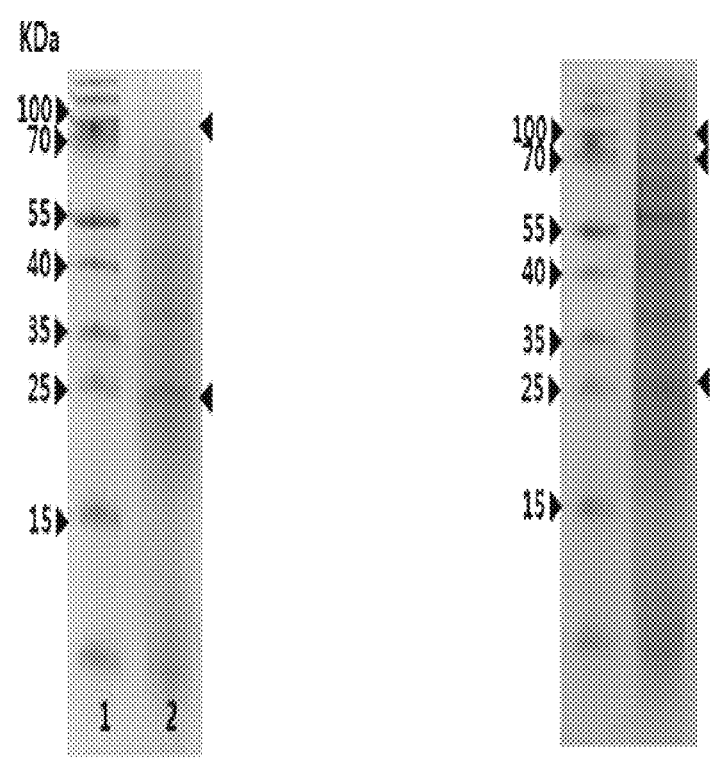
FIG. 4 shows SDS-PAGE results of the expression of the immunocytokine with the human interferon-beta variant according to the present invention (right) and the immunocytokine with human interferon-beta (left). Here, the heavy and light chains of each case are indicated by ☐ (Lane 1 is for a marker).

As a result, as shown in FIG. 4, a light chain was observed at the site of 25 KDa, while an immunocytokine with interferon-beta or an immunocytokine complex with a human interferon-beta variant was observed between 70 KDa and 100 KDa.

Figure 5:
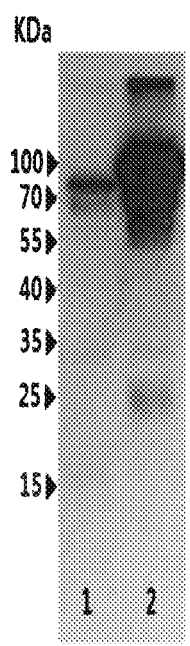
FIG. 5 shows western blot results of the protein expression of the immunocytokine with a human interferon-beta variant according to the present invention (Lane 2) and the immunocytokine with control human interferon β (Lane 1) using anti-human IgG antibody (left) and anti-interferon antibody (right), respectively.
Figure 5:
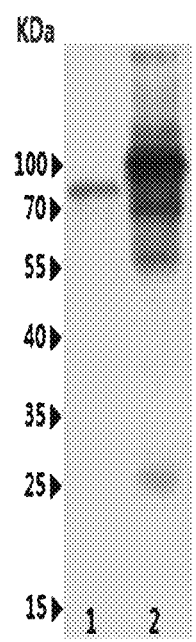
Figure 6:
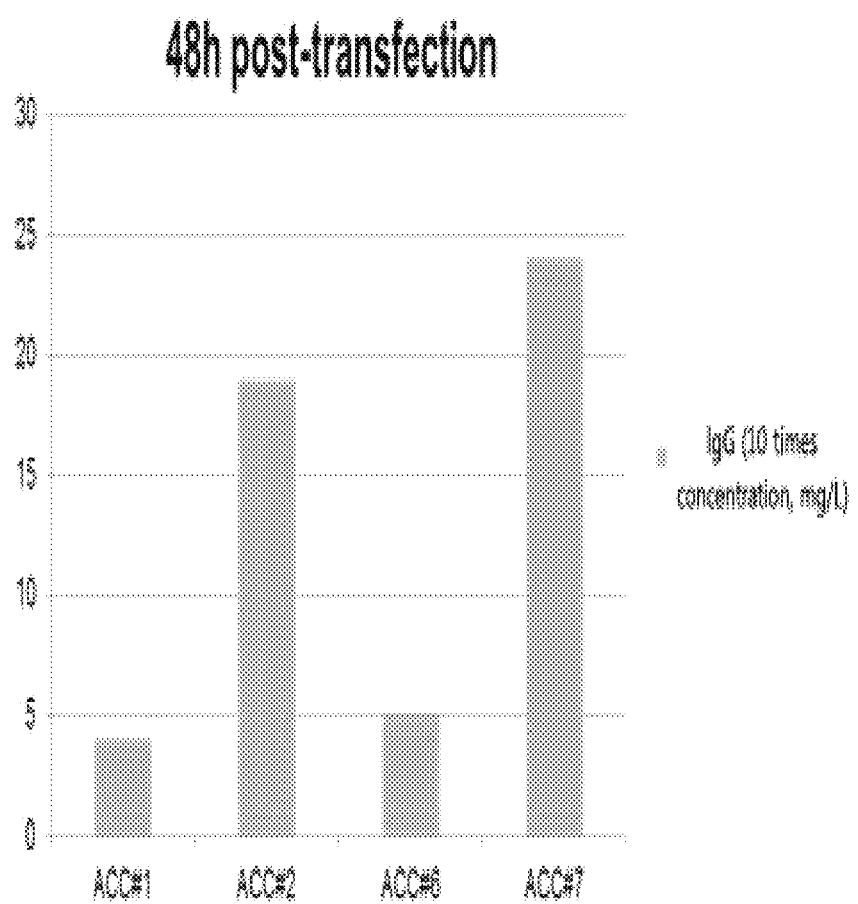
FIG. 6 shows BCA assay results of the expression levels of the immunocytokines produced in host cells (ACC #1: B12 heavy chain-natural interferon, ACC #2: B12 heavy chain-interferon variant, ACC #6: B12 light chain-natural interferon, ACC #7: B12 light chain-interferon variant).

In FIG. 5, Lane 1 indicates an immunocytokine with human interferon-beta, and Lane 2 indicates an immunocytokine with human interferon-beta variant. The Tricine-SDS PAGE and western blotting results confirmed that the expression level of the immunocytokine with the human interferon-beta variant was higher than that of the immunocytokine with human interferon-beta. In addition, for exact comparison of the expression levels, each culture liquid was measured by Cedex Bio (Roche, USA). The results confirmed that the immunocytokine with human interferon-beta showed a concentration below the measurement range (10 mg/L or less), indicating a low level of expression, whereas the immunocytokine with the human interferon-beta variant showed a concentration of about 32 mg/L, indicating a 3-fold increase in the level of expression.

Example 5

Confirmation of Interferon Activity of Immunocytokine Through pSTAT-1 Phosphorylation For confirmation of the interferon function of an immunocytokine in which a human interferon-beta variant is conjugated with B12 antibody according to the present invention, the STAT-1 phosphorylation depending on the treatment with either interferon or an antibody-interferon conjugate was examined.

$3\times10^5$ OVCAR-3 cells were dispensed in each well of a 6-well plate, and cultured for 24 hours at 37.5° C. and 5% $CO_2$. After 24 hours, the cell culture liquid was removed, and a human interferon-beta variant (Carbiferon) was diluted to a concentration of 600 ng/mL and an immunocytokine in which a human interferon-beta variant was conjugated with B12 antibody (ACC) was diluted to a concentration of 600 ng/mL or 1800 ng/mL in the culture liquid, followed by treatment for 1 hour. Thereafter, the plate was collected, and each well was washed three times with PBS, treated with 100 μL of RIPA buffer containing a protease inhibitor and a phosphatase inhibitor, and placed on ice for 30 minutes to dissolve the cells. The dissolved cells were placed in a 1.5-mL tube, and centrifuged at 13,000 rpm at 4° C. and then only the supernatant (lysate) was taken, and collected in a new tube. The protein concentration of the lysate was quantified by BCA assay, and then 30 μg of the lysate was taken, mixed with 5× sample buffer, and boiled at 100° C. for 10 minutes to induce sufficient protein denaturation. The prepared sample was loaded onto a 10% SDS-PAGE gel with a marker, and was allowed to fall at 70 V for 30 minutes and 120 V for 1 hour. Thereafter, the gel was carefully separated, and placed on 3M paper, and then a polyvinylidene difluoride (PVDF) membrane was disposed thereon, and again covered with 3M paper. Thereafter, the resultant structure was immersed in transfer buffer, followed by protein transfer at 100 V for 90 minutes. The membrane was blocked in Tris-buffered saline-Tween 20 (TBS-T, 0.1% Tween 20) containing 5% BSA for 1 hour and 30 minutes, and then the anti-p-STAT1 antibody was prepared by dilution in TBS-T at 1:1000 and the anti-GAPDH antibody was prepared by dilution in TBS-T at 1:3000. The membrane was immersed in the antibody dilution, followed by reaction with shaking at room temperature for 2 hours. After this procedure, the resulting product was washed three times with TBS-T for 10 minutes, and then a horseradish peroxidase (HRP)-conjugated secondary antibody was added thereto, followed by reaction at room temperature for 1 hour. After washing was again conducted, bands were treated with an enhanced chemiluminescence (ECL, Intron) reagent, followed by film development.

Figure 7:
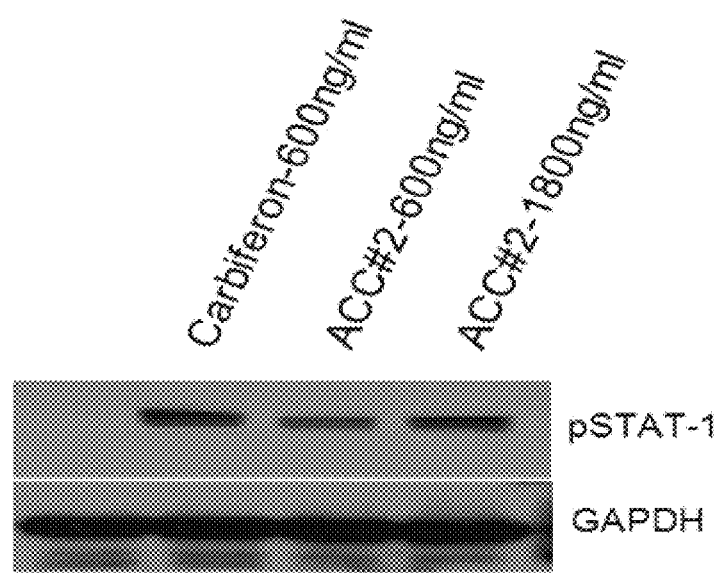
FIG. 7 shows the results of STAT-1 phosphorylation, indicating the interferon activity of the immunocytokine in which the human interferon-beta variant was conjugated to B12 antibody according to the present invention.

The results confirmed that both human interferon-beta (Carbiferon) and immunocytokine treated groups showed pSTAT-1 phosphorylation, indicating that the interferon-beta activity of the immunocytokine in which the human interferon-beta variant (Carbiferon) was conjugated with B12 antibody maintained intact (FIG. 7).

Example 6

Confirmation of Interferon Activity of Immunocytokine Through Cytotoxicity Test

For confirmation of the interferon function of an immunocytokine in which a human interferon-beta variant is conjugated with B12 antibody according to the present invention, the cytotoxicity depending on the treatment with interferon or an antibody-interferon conjugate was examined.

For examination of cytotoxicity, $1\times10^4$ OVCAR-3 cells were dispensed in each well of a 96-well plate, and cultured for 24 hours at 37.5° C. and 5% $CO_2$. After 24 hours, the cell culture liquid was removed, and the cells were treated with the human interferon-beta variant (Carbiferon), B12 antibody, and the immunocytokine in 10-10000 ng/mL, respectively, followed by culture for 24 hours or 48 hours. After the culture for 24 hours or 48 hours, the culture liquid was removed, and PBS washing was conducted two times. WST reagent was mixed with the culture liquid at 1:10, and each well was treated with 10 uL of the mixture, and left at 37.5° C. and 5% $CO_2$ for 2 hours, and then the absorbance was determined at a wavelength of 430 nm.

Figure 8:
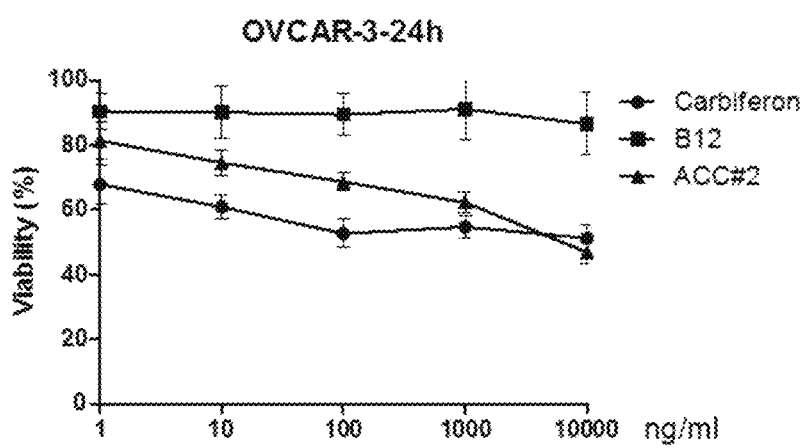
FIG. 8 shows the results wherein cells were treated with the immunocytokine, in which the human interferon-beta variant was conjugated with B12 antibody according to the present invention, for 24 hours, and then the interferon-beta activity of the immunocytokine was investigated through cytotoxicity (Carbiferon: the human interferon-beta variant, B12: B12 antibody, ACC #2: immunocytokine in which the human interferon-beta variant was conjugated with B12 antibody).
Figure 9:
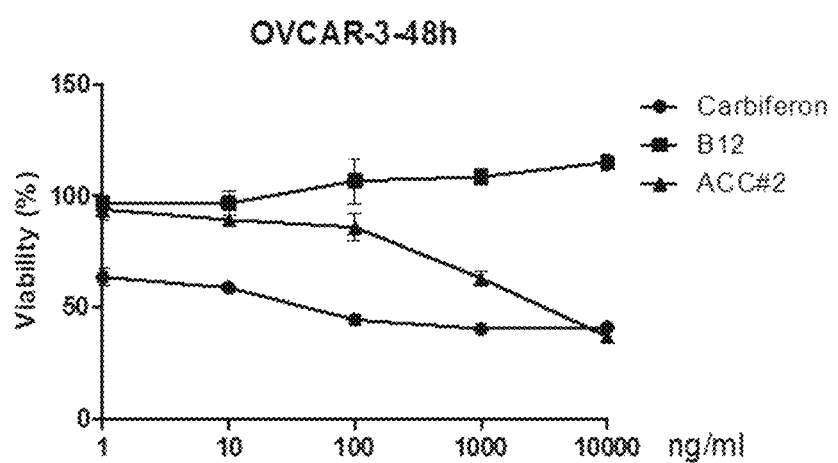
FIG. 9 shows the results wherein cells were treated with the immunocytokine in which the human interferon-beta variant is conjugated with B12 antibody according to the present invention for 48 hours, and then the interferon-beta activity of the immunocytokine was investigated through cytotoxicity (Carbiferon: the human interferon-beta variant, B12: B12 antibody, ACC #2: immunocytokine in which the human interferon-beta variant was conjugated with B12 antibody).

The results confirmed that the cell group treated with only B12 antibody showed no cytotoxicity, whereas the cell groups treated with the human interferon-beta variant or the immunocytokine showed cytotoxicity in a concentration-dependent manner, indicating that the human interferon-beta variant still exhibited interferon activity even in a form of the immunocytokine (FIGS. 8 and 9).

Example 7

Production of Immunocytokines in which Antibody Heavy Chain is Conjugated with Interferon-Beta Variant Immunocytokines in which, besides B12 antibody, ERBB2 (Herceptin) antibody and c-MET antibody were conjugated to an interferon-beta variant, respectively, were prepared as follows.

Figure 10:
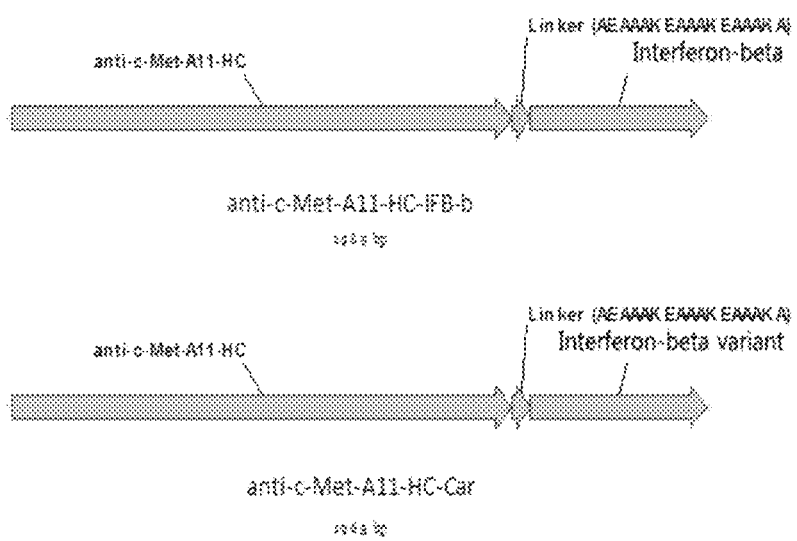
FIG. 10 shows schematic diagrams of immunocytokines produced by linking a rigid helical linker to ERBB2 (Herceptin) antibody (A) and c-MET antibody (B) and then conjugating the human interferon-beta variant thereto, respectively.
Figure 10:
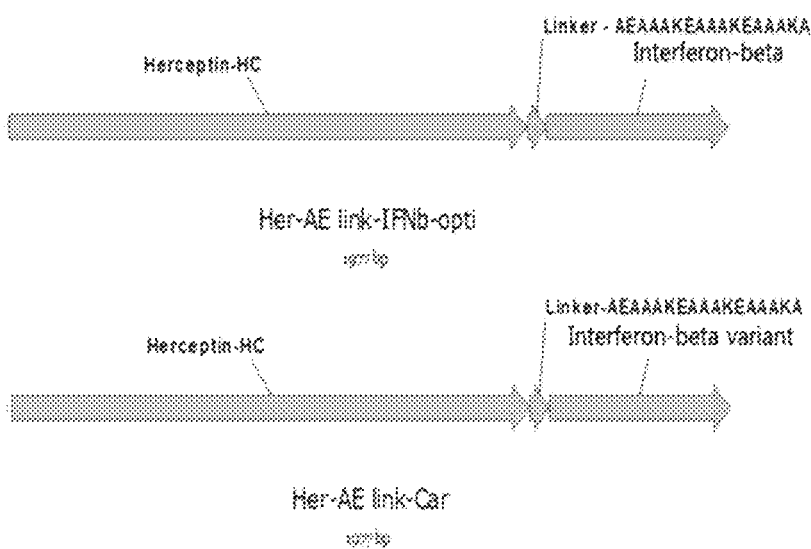

As shown in FIG. 10, a rigid helical linker was linked to a heavy chain region of ERBB2 (Herceptin) antibody and c-MET antibody, respectively. Thereafter, a human interferon-beta variant was conjugated thereto, thereby producing expression cassettes expressing an anti-c-Met immunocytokine (A) and an anti-ERBB2 immunocytokine (B), respectively.

These immunocytokines were cloned into pRBLX2 vectors, respectively, and then each vector was transfected into CHO-S cells, followed by culture for 7 days, thereby inducing expression. The transfection, culture, and the collection of expressed products were conducted as described in Example 4.

When comparing, using CHO-S cells, the expression level between the immuno-cytokine in which the human interferon-beta was conjugated to c-Met antibody or ERBB2 antibody and the immunocytokine in which the human interferon-beta variant was conjugated to the same, it was confirmed that the expression level of the immunocytokine with the human interferon-beta variant was higher than the expression level of the immunocytokine with human interferon-beta, indicating that the immunocytokine with the human interferon-beta variant possesses an excellent interferon activity in comparison with the immunocytokine with human interferon-beta.

As described above, it was verified that the human interferon-beta variant according to the present invention is very favorably expressed in comparison with wild-type interferon-beta.

INDUSTRIAL APPLICABILITY

The immunocytokines with human interferon-beta variants according to the present invention can be used as a target therapeutic agent for a disease (such as multiple sclerosis or cancer) in that the immunocytokines are excellent in both the interferon activity and the characteristics of antibody recognizing a specific antigen, together with their significantly higher production efficiency in comparison with the immunocytokines with natural interferon-beta, leading to their highly industrial applicability.

The invention claimed is:

1. An immunocytokine fusion protein comprising: (a) a human interferon-beta variant comprising a peptide defined by SEQ ID NO: 2; and (b) trastuzumab or an antigen-binding fragment thereof that is linked to the human interferon-beta variant,
wherein the human interferon-beta variant has human interferon-beta activity and comprises an N-linked glycan.

2. The immunocytokine fusion protein of claim 1, wherein the human interferon-beta variant is linked to the trastuzumab or antigen-binding fragment thereof via a peptide linker.

3. The immunocytokine fusion protein of claim 2, wherein the peptide linker comprises the amino acid sequence selected from the group consisting of SEQ ID NO: 5 to SEQ ID NO: 11.

4. The immunocytokine fusion protein of claim 1, wherein the amino acid sequence of the human interferon-beta variant polypeptide is located at a heavy chain C-terminus, a light chain C-terminus, or each of heavy and light chain C-termini of the amino acid sequence of the antibody or fragment thereof.

5. The immunocytokine fusion protein of claim 1, wherein the immunocytokine comprises an amino acid sequence of SEQ ID NO: 12 and 17.

6. A polynucleotide encoding the immunocytokine fusion protein of claim 1.

7. A vector comprising the polynucleotide of claim 6.

8. A host cell transfected with the vector of claim 7.

9. A method for preparing an immunocytokine fusion protein, the method comprising:
(a) providing the host cell of claim 8;
(b) culturing the provided cell; and
(c) preparing an immunocytokine fusion protein by collecting the immunocytokine fusion protein from the cell or a culture medium.

10. A method for increasing a yield of target-specific human interferon-beta, the method comprising:
(a) cloning a polynucleotide encoding an immunocytokine fusion protein of claim 1 into an expression vector;
(b) introducing the expression vector into a host cell;
(c) culturing the host cell; and
(d) collecting the immunocytokine fusion protein from the cell or a culture medium.

* * * * *

SEQUENCE LISTING

```
<160> NUMBER OF SEQ ID NOS: 17

<210> SEQ ID NO 1
<211> LENGTH: 166
<212> TYPE: PRT
<213> ORGANISM: Artificial Sequence
<220> FEATURE:
<223> OTHER INFORMATION: Human interferon-beta

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 166
<212> TYPE: PRT
<213> ORGANISM: Artificial Sequence
```

```
<220> FEATURE:
<223> OTHER INFORMATION: Interferon beta mutein - R27T protein

<400> SEQUENCE: 2

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Thr Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 3
<211> LENGTH: 166
<212> TYPE: PRT
<213> ORGANISM: Artificial Sequence
<220> FEATURE:
<223> OTHER INFORMATION: Interferon beta mutein - R27S protein

<400> SEQUENCE: 3

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Ser Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
```

```
                165

<210> SEQ ID NO 4
<211> LENGTH: 171
<212> TYPE: PRT
<213> ORGANISM: Artificial Sequence
<220> FEATURE:
<223> OTHER INFORMATION: Interferon beta mutein - GNITV protein

<400> SEQUENCE: 4

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn Gly Asn Ile Thr Val
                165                 170

<210> SEQ ID NO 5
<211> LENGTH: 5
<212> TYPE: PRT
<213> ORGANISM: Artificial Sequence
<220> FEATURE:
<223> OTHER INFORMATION: Linker

<400> SEQUENCE: 5

Gly Gly Gly Gly Ser
1               5

<210> SEQ ID NO 6
<211> LENGTH: 15
<212> TYPE: PRT
<213> ORGANISM: Artificial Sequence
<220> FEATURE:
<223> OTHER INFORMATION: Linker

<400> SEQUENCE: 6

Gly Gly Gly Gly Ser Gly Gly Gly Ser Gly Gly Gly Ser Gly
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: GGGGSGGGGSGGGGSGGGGS linker
```

```
<400> SEQUENCE: 7

Gly Gly Gly Gly Ser Gly Gly Gly Gly Ser Gly Gly Gly Gly Ser Gly
1               5                   10                  15

Gly Gly Gly Ser
            20

<210> SEQ ID NO 8
<211> LENGTH: 4
<212> TYPE: PRT
<213> ORGANISM: Artificial Sequence
<220> FEATURE:
<223> OTHER INFORMATION: ASGG linker

<400> SEQUENCE: 8

Gly Gly Gly Ser
1

<210> SEQ ID NO 9
<211> LENGTH: 15
<212> TYPE: PRT
<213> ORGANISM: Artificial Sequence
<220> FEATURE:
<223> OTHER INFORMATION: GVGGSGGGGSGGGGS linker

<400> SEQUENCE: 9

Gly Val Gly Gly Ser Gly Gly Gly Gly Ser Gly Gly Gly Gly Ser
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: DDDDK linker

<400> SEQUENCE: 10

Asp Asp Asp Asp Lys
1               5

<210> SEQ ID NO 11
<211> LENGTH: 17
<212> TYPE: PRT
<213> ORGANISM: Artificial Sequence
<220> FEATURE:
<223> OTHER INFORMATION: AEAAAKEAAAKEAAAKA  linker

<400> SEQUENCE: 11

Ala Glu Ala Ala Ala Lys Glu Ala Ala Ala Lys Glu Ala Ala Ala Lys
1               5                   10                  15

Ala

<210> SEQ ID NO 12
<211> LENGTH: 627
<212> TYPE: PRT
<213> ORGANISM: Artificial Sequence
<220> FEATURE:
<223> OTHER INFORMATION: Immunocytokine 1

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Ser Trp Val Arg Gln Ala Pro Gly Lys Gly Leu Glu Trp Val
```

```
                35                  40                  45
Ser Val Ile Ser His Asp Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Ala Arg Val Cys Thr Pro Lys Arg Cys Tyr Ser Tyr Asp
                100                 105                 110
Ala Met Asp Val Trp Gly Gln Gly Thr Leu Val Thr Val Ser Ser Ala
                115                 120                 125
Ser Thr Lys Gly Pro Ser Val Phe Pro Leu Ala Pro Ser Ser Lys Ser
130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
                180                 185                 190
Ser Ser Val Val Thr Val Pro Ser Ser Ser Leu Gly Thr Gln Thr Tyr
                195                 200                 205
Ile Cys Asn Val Asn His Lys Pro Ser Asn Thr Lys Val Asp Lys Lys
210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
                260                 265                 270
Val Val Asp Val Ser His Glu Asp Pro Glu Val Lys Phe Asn Trp Tyr
                275                 280                 285
Val Asp Gly Val Glu Val His Asn Ala Lys Thr Lys Pro Arg Glu Glu
                290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
                340                 345                 350
Pro Arg Glu Pro Gln Val Tyr Thr Leu Pro Pro Ser Arg Asp Glu Leu
                355                 360                 365
Thr Lys Asn Gln Val Ser Leu Thr Cys Leu Val Lys Gly Phe Tyr Pro
370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
                420                 425                 430
Phe Ser Cys Ser Val Met His Glu Ala Leu His Asn His Tyr Thr Gln
                435                 440                 445
Lys Ser Leu Ser Leu Ser Pro Gly Lys Gly Gly Gly Gly Ser Ser Tyr
450                 455                 460
```

```
Asn Leu Leu Gly Phe Leu Gln Arg Ser Ser Asn Phe Gln Cys Gln Lys
465                 470                 475                 480

Leu Leu Trp Gln Leu Asn Gly Thr Leu Glu Tyr Cys Leu Lys Asp Arg
            485                 490                 495

Met Asn Phe Asp Ile Pro Glu Glu Ile Lys Gln Leu Gln Gln Phe Gln
                500                 505                 510

Lys Glu Asp Ala Ala Leu Thr Ile Tyr Glu Met Leu Gln Asn Ile Phe
            515                 520                 525

Ala Ile Phe Arg Gln Asp Ser Ser Thr Gly Trp Asn Glu Thr Ile
530                 535                 540

Val Glu Asn Leu Leu Ala Asn Val Tyr His Gln Ile Asn His Leu Lys
545                 550                 555                 560

Thr Val Leu Glu Glu Lys Leu Glu Lys Glu Asp Phe Thr Arg Gly Lys
                565                 570                 575

Leu Met Ser Ser Leu His Leu Lys Arg Tyr Tyr Gly Arg Ile Leu His
            580                 585                 590

Tyr Leu Lys Ala Lys Glu Tyr Ser His Cys Ala Trp Thr Ile Val Arg
        595                 600                 605

Val Glu Ile Leu Arg Asn Phe Tyr Phe Ile Asn Arg Leu Thr Gly Tyr
    610                 615                 620

Leu Arg Asn
625

<210> SEQ ID NO 13
<211> LENGTH: 386
<212> TYPE: PRT
<213> ORGANISM: Artificial Sequence
<220> FEATURE:
<223> OTHER INFORMATION: Immunocytokine 2

<400> SEQUENCE: 13

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Asn Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Lys Ser Tyr Ser Cys Gln Val Thr His Glu Gly Ser Thr Val Glu Lys
            195                 200                 205

Thr Val Ala Pro Ala Glu Cys Ser Gly Gly Gly Ser Ser Tyr Asn
210                 215                 220

Leu Leu Gly Phe Leu Gln Arg Ser Ser Asn Phe Gln Cys Gln Lys Leu
225                 230                 235                 240

Leu Trp Gln Leu Asn Gly Thr Leu Glu Tyr Cys Leu Lys Asp Arg Met
            245                 250                 255

Asn Phe Asp Ile Pro Glu Glu Ile Lys Gln Leu Gln Gln Phe Gln Lys
            260                 265                 270

Glu Asp Ala Ala Leu Thr Ile Tyr Glu Met Leu Gln Asn Ile Phe Ala
            275                 280                 285

Ile Phe Arg Gln Asp Ser Ser Ser Thr Gly Trp Asn Glu Thr Ile Val
            290                 295                 300

Glu Asn Leu Leu Ala Asn Val Tyr His Gln Ile Asn His Leu Lys Thr
305                 310                 315                 320

Val Leu Glu Glu Lys Leu Glu Lys Glu Asp Phe Thr Arg Gly Lys Leu
            325                 330                 335

Met Ser Ser Leu His Leu Lys Arg Tyr Tyr Gly Arg Ile Leu His Tyr
            340                 345                 350

Leu Lys Ala Lys Glu Tyr Ser His Cys Ala Trp Thr Ile Val Arg Val
            355                 360                 365

Glu Ile Leu Arg Asn Phe Tyr Phe Ile Asn Arg Leu Thr Gly Tyr Leu
            370                 375                 380

Arg Asn
385

<210> SEQ ID NO 14
<211> LENGTH: 648
<212> TYPE: PRT
<213> ORGANISM: Artificial Sequence
<220> FEATURE:
<223> OTHER INFORMATION: anti c-Met interferon-beta

<400> SEQUENCE: 14

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Gly Tyr Tyr Met Ser Trp Val Arg Gln Ala Pro Gly Lys Gly
50                  55                  60

Leu Glu Trp Val Ser Ala Ile Ser His Ser Gly Gly Ser Thr Tyr Tyr
65                  70                  75                  80

Ala Asp Ser Val Lys Gly Arg Phe Thr Ile Ser Arg Asp Asn Ser Lys
            85                  90                  95

Asn Thr Leu Tyr Leu Gln Met Asn Ser Leu Arg Ala Glu Asp Thr Ala
        100                 105                 110

Val Tyr Tyr Cys Ala Lys Trp Gly Pro Ala Phe Asp Tyr Trp Gly Gln
    115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160
```

```
Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys Ala Glu Ala Ala Ala Lys Glu Ala Ala Ala Lys Glu Ala Ala
465                 470                 475                 480

Ala Lys Ala Ser Tyr Asn Leu Leu Gly Phe Leu Gln Arg Ser Ser Asn
                485                 490                 495

Phe Gln Cys Gln Lys Leu Leu Trp Gln Leu Asn Gly Arg Leu Glu Tyr
                500                 505                 510

Cys Leu Lys Asp Arg Met Asn Phe Asp Ile Pro Glu Glu Ile Lys Gln
            515                 520                 525

Leu Gln Gln Phe Gln Lys Glu Asp Ala Ala Leu Thr Ile Tyr Glu Met
            530                 535                 540

Leu Gln Asn Ile Phe Ala Ile Phe Arg Gln Asp Ser Ser Ser Thr Gly
545                 550                 555                 560

Trp Ala Glu Thr Ile Val Glu Asn Leu Leu Ala Asn Val Tyr His Gln
                565                 570                 575
```

```
Ile Asn His Leu Lys Thr Val Leu Glu Glu Lys Leu Glu Lys Glu Asp
                580                 585                 590

Phe Thr Arg Gly Lys Leu Met Ser Ser Leu His Leu Lys Arg Tyr Tyr
            595                 600                 605

Gly Arg Ile Leu His Tyr Leu Lys Ala Lys Glu Tyr Ser His Cys Ala
        610                 615                 620

Trp Thr Ile Val Arg Val Glu Ile Leu Arg Asn Phe Tyr Phe Ile Asn
625                 630                 635                 640

Arg Leu Thr Gly Tyr Leu Arg Asn
                645

<210> SEQ ID NO 15
<211> LENGTH: 648
<212> TYPE: PRT
<213> ORGANISM: Artificial Sequence
<220> FEATURE:
<223> OTHER INFORMATION: anti c-Met interferon-beta mutein

<400> SEQUENCE: 15

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Gly Tyr Tyr Met Ser Trp Val Arg Gln Ala Pro Gly Lys Gly
    50                  55                  60

Leu Glu Trp Val Ser Ala Ile Ser His Ser Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Trp Gly Pro Ala Phe Asp Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285
```

```
Asp Pro Glu Val Lys Phe Asn Trp Tyr Val Asp Gly Val Glu Val His
        290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys Ala Glu Ala Ala Ala Lys Glu Ala Ala Ala Lys Glu Ala Ala
465                 470                 475                 480
Ala Lys Ala Ser Tyr Asn Leu Leu Gly Phe Leu Gln Arg Ser Ser Asn
                485                 490                 495
Phe Gln Cys Gln Lys Leu Leu Trp Gln Leu Asn Gly Thr Leu Glu Tyr
            500                 505                 510
Cys Leu Lys Asp Arg Met Asn Phe Asp Ile Pro Glu Glu Ile Lys Gln
        515                 520                 525
Leu Gln Gln Phe Gln Lys Glu Asp Ala Ala Leu Thr Ile Tyr Glu Met
    530                 535                 540
Leu Gln Asn Ile Phe Ala Ile Phe Arg Gln Asp Ser Ser Ser Thr Gly
545                 550                 555                 560
Trp Asn Glu Thr Ile Val Glu Asn Leu Leu Ala Asn Val Tyr His Gln
                565                 570                 575
Ile Asn His Leu Lys Thr Val Leu Glu Glu Lys Leu Glu Lys Glu Asp
            580                 585                 590
Phe Thr Arg Gly Lys Leu Met Ser Ser Leu His Leu Lys Arg Tyr Tyr
        595                 600                 605
Gly Arg Ile Leu His Tyr Leu Lys Ala Lys Glu Tyr Ser His Cys Ala
    610                 615                 620
Trp Thr Ile Val Arg Val Glu Ile Leu Arg Asn Phe Tyr Phe Ile Asn
625                 630                 635                 640
Arg Leu Thr Gly Tyr Leu Arg Asn
                645

<210> SEQ ID NO 16
<211> LENGTH: 652
<212> TYPE: PRT
<213> ORGANISM: Artificial Sequence
<220> FEATURE:
<223> OTHER INFORMATION: anti ERBB2 interferon-beta

<400> SEQUENCE: 16
```

```
Met Glu Thr Asp Thr Leu Leu Leu Trp Val Leu Leu Leu Trp Val Pro
  1               5                  10                  15

Gly Ser Thr Gly Glu Val Gln Leu Val Glu Ser Gly Gly Gly Leu Val
             20                  25                  30

Gln Pro Gly Gly Ser Leu Arg Leu Ser Cys Ala Ala Ser Gly Phe Asn
             35                  40                  45

Ile Lys Asp Thr Tyr Ile His Trp Val Arg Gln Ala Pro Gly Lys Gly
 50                  55                  60

Leu Glu Trp Val Ala Arg Ile Tyr Pro Thr Asn Gly Tyr Thr Arg Tyr
 65                  70                  75                  80

Ala Asp Ser Val Lys Gly Arg Phe Thr Ile Ser Ala Asp Thr Ser Lys
                 85                  90                  95

Asn Thr Ala Tyr Leu Gln Met Asn Ser Leu Arg Ala Glu Asp Thr Ala
                100                 105                 110

Val Tyr Tyr Cys Ser Arg Trp Gly Gly Asp Gly Phe Tyr Ala Met Asp
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
```

```
            420                 425                 430
Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Lys Ala Glu Ala Ala Lys Glu Ala Ala Ala
465                 470                 475                 480

Lys Glu Ala Ala Ala Lys Ala Ser Tyr Asn Leu Leu Gly Phe Leu Gln
                485                 490                 495

Arg Ser Ser Asn Phe Gln Cys Gln Lys Leu Leu Trp Gln Leu Asn Gly
                500                 505                 510

Arg Leu Glu Tyr Cys Leu Lys Asp Arg Met Asn Phe Asp Ile Pro Glu
                515                 520                 525

Glu Ile Lys Gln Leu Gln Gln Phe Gln Lys Glu Asp Ala Ala Leu Thr
                530                 535                 540

Ile Tyr Glu Met Leu Gln Asn Ile Phe Ala Ile Phe Arg Gln Asp Ser
545                 550                 555                 560

Ser Ser Thr Gly Trp Ala Glu Thr Ile Val Glu Asn Leu Leu Ala Asn
                565                 570                 575

Val Tyr His Gln Ile Asn His Leu Lys Thr Val Leu Glu Glu Lys Leu
                580                 585                 590

Glu Lys Glu Asp Phe Thr Arg Gly Lys Leu Met Ser Ser Leu His Leu
                595                 600                 605

Lys Arg Tyr Tyr Gly Arg Ile Leu His Tyr Leu Lys Ala Lys Glu Tyr
                610                 615                 620

Ser His Cys Ala Trp Thr Ile Val Arg Val Glu Ile Leu Arg Asn Phe
625                 630                 635                 640

Tyr Phe Ile Asn Arg Leu Thr Gly Tyr Leu Arg Asn
                645                 650

<210> SEQ ID NO 17
<211> LENGTH: 652
<212> TYPE: PRT
<213> ORGANISM: Artificial Sequence
<220> FEATURE:
<223> OTHER INFORMATION: anti ERBB2 interferon-beta mutein

<400> SEQUENCE: 17

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
                35                  40                  45

Ile Lys Asp Thr Tyr Ile His Trp Val Arg Gln Ala Pro Gly Lys Gly
        50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
                100                 105                 110

Val Tyr Tyr Cys Ser Arg Trp Gly Gly Asp Gly Phe Tyr Ala Met Asp
                115                 120                 125

Tyr Trp Gly Gln Gly Thr Leu Val Thr Val Ser Ser Ala Ser Thr Lys
```

-continued

```
              130                 135                 140
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
                370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys Ala Glu Ala Ala Lys Glu Ala Ala
465                 470                 475                 480

Lys Glu Ala Ala Ala Lys Ala Ser Tyr Asn Leu Leu Gly Phe Leu Gln
                485                 490                 495

Arg Ser Ser Asn Phe Gln Cys Gln Lys Leu Leu Trp Gln Leu Asn Gly
                500                 505                 510

Thr Leu Glu Tyr Cys Leu Lys Asp Arg Met Asn Phe Asp Ile Pro Glu
                515                 520                 525

Glu Ile Lys Gln Leu Gln Gln Phe Gln Lys Glu Asp Ala Ala Leu Thr
                530                 535                 540

Ile Tyr Glu Met Leu Gln Asn Ile Phe Ala Ile Phe Arg Gln Asp Ser
545                 550                 555                 560
```

```
Ser Ser Thr Gly Trp Asn Glu Thr Ile Val Glu Asn Leu Leu Ala Asn
            565                 570                575

Val Tyr His Gln Ile Asn His Leu Lys Thr Val Leu Glu Glu Lys Leu
            580             585                 590

Glu Lys Glu Asp Phe Thr Arg Gly Lys Leu Met Ser Ser Leu His Leu
        595                 600             605

Lys Arg Tyr Tyr Gly Arg Ile Leu His Tyr Leu Lys Ala Lys Glu Tyr
    610                 615             620

Ser His Cys Ala Trp Thr Ile Val Arg Val Glu Ile Leu Arg Asn Phe
625                 630             635                 640

Tyr Phe Ile Asn Arg Leu Thr Gly Tyr Leu Arg Asn
            645                 650
```